(12) United States Patent
Zhang (10) Patent No.: US 11,195,114 B2
(45) Date of Patent: Dec. 7, 2021

(54) MEDICAL DATA ANALYSIS METHOD AND DEVICE AS WELL AS COMPUTER-READABLE STORAGE MEDIUM

(71) Applicant: BOE TECHNOLOGY GROUP CO., LTD., Beijing (CN)

(72) Inventor: Zhenzhong Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 904 days.

(21) Appl. No.: 15/768,825

(22) PCT Filed: Jul. 7, 2017

(86) PCT No.: PCT/CN2017/092186
§ 371 (c)(1),
(2) Date: Apr. 16, 2018

(87) PCT Pub. No.: WO2018/133340
PCT Pub. Date: Jul. 26, 2018

(65) Prior Publication Data
US 2019/0057316 A1    Feb. 21, 2019

(30) Foreign Application Priority Data
Jan. 19, 2017  (CN) ...................... 201710038539.X (51) Int. Cl.
*G06N 7/00*    (2006.01)
*G16H 50/20*   (2018.01)
(Continued)

(52) U.S. Cl.
CPC ............. *G06N 7/005* (2013.01); *G06N 5/022* (2013.01); *G16H 50/20* (2018.01); *G16H 50/30* (2018.01); *G16H 70/20* (2018.01); *G06N 20/00* (2019.01)

(58) Field of Classification Search
CPC ........ G06N 7/005; G06N 20/00; G06N 5/022; G16H 50/30; G16H 50/20; G16H 70/20
(Continued)

(56) References Cited

U.S. PATENT DOCUMENTS

| 8,015,136 B1* | 9/2011 | Baker | G16H 10/60 706/45 |
| 2003/0009333 A1* | 1/2003 | Sharma | G10L 15/04 704/246 |

(Continued)

FOREIGN PATENT DOCUMENTS

| CN | 102184314 A | 9/2011 |
| CN | 103020454 A | 4/2013 |

(Continued)

OTHER PUBLICATIONS

Extended European Search Report received for EP Patent Application No. 17859359.6, dated Dec. 3, 2020, 10 pages.

(Continued)

*Primary Examiner* — Dave Misir
(74) *Attorney, Agent, or Firm* — Womble Bond Dickinson (US) LLP (57) ABSTRACT

The present disclosure provides a medical data analysis method and device. The method comprises locating a semantic subspace of the subject in a medical data set by taking the physical parameter as a feature; and analyzing the probability $P_1$ of the subject being in the semantic subspace that the subject belongs to by judging the semantic consistency of the semantic subspace where the physical parameter of the subject exists. In addition, it is also possible to analyze the probability $P_2$ of the subject being in the node that the subject belongs to based on the evidence transference score of the physical parameter of the subject on the medical knowledge graph. $P=\alpha \times P_1+(1-\alpha) \times P_2$ The probability P of the subject being in the semantic subspace or node that the (Continued)

subject belongs to can be determined by $P=\alpha \times P_1+(1-\alpha) \times P_2$, wherein $\alpha$ is a reconciling parameter, $0<\alpha<1$. Through these solutions, the analysis accuracy and efficiency can be improved and the cost can be decreased.

15 Claims, 5 Drawing Sheets

(51) Int. Cl.
*G16H 70/20* (2018.01)
*G16H 50/30* (2018.01)
*G06N 5/02* (2006.01)
*G06N 20/00* (2019.01)

(58) Field of Classification Search
USPC .......................................................... 706/55
See application file for complete search history.

(56) References Cited

U.S. PATENT DOCUMENTS

| | | | |
|---|---|---|---|
| 2009/0024332 A1* | 1/2009 | Karlov | G16H 50/70 702/19 |
| 2009/0259494 A1* | 10/2009 | Feder | G16H 10/60 705/3 |
| 2011/0112380 A1* | 5/2011 | Robinson | A61B 5/0002 600/300 |
| 2014/0168246 A1 | 6/2014 | Tzao et al. | |
| 2017/0344711 A1* | 11/2017 | Liu | G16H 50/20 |

FOREIGN PATENT DOCUMENTS

| | | | | |
|---|---|---|---|---|
| CN | 104156905 A | | 11/2014 | |
| CN | 103020454 A | * | 4/2015 | ............. G06F 19/00 |
| CN | 104484844 A | | 4/2015 | |
| CN | 104915561 A | * | 9/2015 | ............. G06F 19/00 |
| CN | 105653859 A | | 6/2016 | |
| CN | 105738109 A | | 7/2016 | |
| CN | 108335755 A | | 7/2018 | |
| WO | 2018/228151 A1 | | 12/2018 | |

OTHER PUBLICATIONS

Zhao et al., "Multi-View Neural Network Integrating Knowledge for Patient Self-Diagnosis", ICMLSC 2019, pp. 33-38.
Office Action received for Chinese Patent Application No. 201710038539.X, dated Mar. 29, 2021, 25 pages (12 pages of English Translation and 13 pages of Office Action).

* cited by examiner

Fig.1

Different
shapes represent
different diseases

MEDICAL DATA ANALYSIS METHOD AND DEVICE AS WELL AS COMPUTER-READABLE STORAGE MEDIUM

RELATED APPLICATIONS

The present application is the U.S. national phase entry of PCT/CN2017/092186 with an International filing date of Jul. 7, 2017, which claims the benefit of Chinese Patent Application No. 201710038539.X, filed on Jan. 19, 2017, the entire disclosure of which is incorporated herein by reference.

TECHNICAL FIELD

The present disclosure relates to a data analysis method and device, and more particularly, to a data analysis method and device based on medical data and/or a medical knowledge graph.

BACKGROUND ART

The latest study of Advisory Board Company shows: in the next ten years, the costs spent by the public at medical institutions will increase by 5% each year. Thus, for the sake of survival and development, medical institutions shall try every means to reduce the costs by 20%. An effective way to achieve this goal is to diagnose critical diseases as early as possible by making use of big data analysis technologies.

As we all know, if warning signals of critical diseases can be discovered at an early stage, the treatment process will be much simpler at a cheaper price and with better recovery than a late diagnosis. According to EMC's report, 22% of medical institutions increase the rate of diagnosing critical diseases at an early stage by means of data analysis technologies. Some medical institutions in the United States have saved considerable costs and improved the quality of care to patients through data analysis: Meriter Health Service Company in Madison, Wisconson, U.S. has deployed a set of commercial intelligent solutions to integrate data from analytic systems and electronic health record (EHR) systems and provide tremendous, practically significant information for administrative staff and clinical doctors. Abundant information provides accurate reference data for plastic surgeons in Meriter Co., and also provides the basis for doctors to select suitable prostheses for patients. With the help of the information, hospitals can utilize medical expenses more effectively—Meriter Co. has saved about one million USD in a short period of eight months after utilization of data analysis.

SUMMARY

According to one aspect, there is provided a medical data analysis method, comprising:

receiving a physical parameter of a subject;

locating a semantic subspace of the subject in a medical data set by taking the physical parameter as a feature; and analyzing a probability $P_1$ of the subject being in the semantic subspace that the subject belongs to by analyzing the semantic consistency of the semantic subspace where the physical parameter of the subject exists;

analyzing a probability $P_2$ of the subject being in the node that the subject belongs to based on the evidence transference score of the physical parameter of the subject on the medical knowledge graph; and determining the probability P of the subject being in the semantic subspace or node that the subject belongs to based on the probability $P_1$ and probability $P_2$:

$$P=\alpha \times P_1+(1-\alpha)\times P_2,$$

wherein $\alpha$ is a reconciling parameter, $0\leq\alpha\leq 1$.

In an embodiment, the locating a semantic subspace of the subject in a medical data set by taking the physical parameter as a feature comprises:

setting up a vector h according to the physical parameter of the subject to represent the physical parameter; and locating the semantic subspace of the subject in the medical data set by taking the physical parameter as a feature, wherein a matrix D is used to represent a collection of cases in a data set, $D=[D_1, D_2, \ldots, D_M]$, $D_i$ represents an i-th semantic subspace, $1\leq i\leq M$ represents the number of semantic subspaces, the locating comprising: acquiring X by an equation h=DX, wherein X is a coefficient vector indicative of the distribution of the vector h in each semantic subspace; and the analyzing semantic consistency of the semantic subspace where the physical parameter of the subject exists comprises judging semantic consistency of a semantic subspace that the vector h is in.

In an embodiment, the locating a semantic subspace of the subject in a medical data set by taking the physical parameter as a feature further comprises:

solving the equation h=DX by way of a sparsest solution to thereby determine the semantic subspace where the subject exists; and determining which semantic subspace has the most contents of h according to a value of each element in the coefficient vector X, thereby determining which semantic subspace h is most likely to exist.

In an embodiment, the sparsest solution comprises:

solving $x^*=\arg\min\|X\|_1$ wherein X satisfies $\|DX-h\|_2\leq\varepsilon$, and wherein $\|\cdot\|_1$ is L1 paradigm, $\|\cdot\|_2$ is L2 paradigm, and $\varepsilon$ is a predetermined parameter, wherein cases corresponding to non-zero dimensions in the obtained solutions $x^*$ constitute the semantic subspace that h is in.

In an embodiment, the the semantic consistency of the semantic subspace where the vector h exists further comprises:

calculating the semantic consistency between the semantic subspace that h is in and the semantic subspace $D_i$ by the following equations:

$$C_i = \frac{\|h_i\|_2^2}{\sum_j \|h_j\|_2^2 + \|\eta\|_2^2} (i=1, 2, \ldots, M)$$

$$C_\eta = \frac{\|\eta\|_2^2}{\sum_j \|h_j\|_2^2 + \|\eta\|_2^2},$$

wherein $h=h_1+h_2+\ldots+h_M+\eta$, $h_i=D\delta_i(X)$, $\eta$ is an error, $\delta_i(X)$ represents a column vector obtained by multiplying the elements of the coefficient vector X belonging to the dimensions of the semantic subspace $D_i$ by 1 and multiplying those belonging to the rest dimensions by 0.

In an embodiment, the method further comprises:

outputting the maximum value of $C_1, C_2, \ldots, C_M, c_\eta$ as the probability $P_1$ of the subject being in the semantic subspace that the subject belongs to.

In an embodiment, wherein the analyzing a probability $P_2$ of the subject being in a node that the subject belongs to based on the evidence transference score of the physical parameter of the subject on the medical knowledge graph comprises:

accessing the medical knowledge graph to obtain a portion of the medical knowledge graph in relation to the subject, the portion of the medical knowledge graph comprising a plurality of nodes $V=\{v_1, v_2, \ldots, v_N\}$ and an initial evidence score set $p_0=[p_{0,1}, p_{0,2}, \ldots, p_{0,N}]$ for said plurality of nodes, wherein N indicates the number of said plurality of nodes, $$\sum_{i=1}^{N} p_{0,i} = 1,$$

each node $v_i$ represents one physical parameter or one relevant category, i is an index for indexing the node, and $p_{0,i}$ represents the initial evidence score of the node $v_i$;

determining a final evidence score set p for said plurality of nodes based on an evidence transference score of a physical parameter of the subject on the portion of the medical knowledge graph; and obtaining the probability $P_2$ of the subject being in the node that the subject belongs to based on the final evidence score of each node in the the final evidence score set p.

In an embodiment, the determining the final evidence score set p for said plurality of nodes further comprises:

performing iterative computation by the following equation to determine the final evidence score set p for said plurality of nodes:

$$p_t=(1-d)\times p_0+d\times p_{t-1}\times W,$$

wherein d is a damping coefficient, 0<d<1;

$$W = \begin{bmatrix} l_{11} & l_{12} & \ldots & l_{1N} \\ l_{21} & l_{22} & \ldots & l_{2N} \\ \vdots & \vdots & \ldots & \vdots \\ l_{N1} & l_{N2} & \ldots & l_{NN} \end{bmatrix}, l_{ij} = \frac{w_{i,j}}{\sum_{k=1}^{N} w_{i,k}},$$

$w_{i,j}$ represents a weight of an edge $e_{i,j}$ connecting nodes $v_i$, $v_j$ in V, $p_{t-1}$ and $p_t$ represent an evidence score set for said plurality of nodes before t iterative computation and that after t iterative computation respectively, the final evidence score set p is determined as $p_t$ after the iterative computation is terminated.

In an embodiment, the condition for terminating the iterative computation is that $p_t$ does not change any longer or reaches a predetermined maximum number of iterations in the iterative computation.

In an embodiment, the determining the final evidence score set p for said plurality of nodes further comprises:

determining the final evidence score set p for said plurality of nodes by the following equation:

$$p=(1-d)\times p_0\times(I-d\times W)^{-1},$$

wherein d is a damping coefficient, 0<d<1; I is an N×N unit matrix, $$W = \begin{bmatrix} l_{11} & l_{12} & \ldots & l_{1N} \\ l_{21} & l_{22} & \ldots & l_{2N} \\ \vdots & \vdots & \ldots & \vdots \\ l_{N1} & l_{N2} & \ldots & l_{NN} \end{bmatrix}, l_{ij} = \frac{w_{i,j}}{\sum_{k=1}^{N} w_{i,k}},$$

$w_{i,j}$ represents the weight of an edge $e_{i,j}$ connecting the nodes $v_i$, $v_j$ in V.

In an embodiment, the analyzing the probability $P_2$ of the subject being in the node that the subject belongs to based on the final evidence score of each node in the final evidence score set p further comprises:

determining the probability of falling into each node by calculating the percentage of the final score of each disease node in V in the sum of the final scores of all disease nodes in V; and outputting the maximum probability in the probability as the probability $P_2$ of the subject being in the node that the subject belongs to.

According to another aspect, there is provided a medical data analysis device, comprising:

a receiver configured to receive a physical parameter of a subject;

a subspace locator configured to locate a semantic subspace of the subject in a medical data set by taking the physical parameter as a feature; and a first analyzer configured to analyze the probability $P_1$ of the subject being in the semantic subspace that the subject belongs to by analyzing the semantic consistency of the semantic subspace where the physical parameter of the subject exists;

a second analyzer configured to analyze the probability $P_2$ of the subject being in the node that the subject belongs to based on the evidence transference score of the physical parameter of the subject on the medical knowledge graph; and a reconciler configured to determine the probability P of the subject being in the semantic subspace or node that the subject belongs to based on the probability $P_1$ and probability $P_2$:

$$P=\alpha\times P_1+(1-\alpha)\times P_2,$$

wherein $\alpha$ is a reconciling parameter, $0\le\alpha\le1$.

In an embodiment, the receiver is configured to set up a vector h according to the physical parameter to represent the physical parameter;

the subspace locator is configured to acquire X by an equation h=DX, wherein D is a matrix used to represent a collection of cases in a data set, $D=[D_1, D_2, \ldots, D_M]$, $D_i$ represents an i-th semantic subspace, $1\le i\le M$ represents the number of semantic subspaces, and X is a coefficient vector indicative of the distribution of the vector h in each semantic subspace; and the first analyzer is configured to analyze semantic consistency of the semantic subspace where the physical parameter of the subject exists by judging the semantic consistency of the semantic subspace where the vector h exists.

In an embodiment, the subspace locator is further configured to:

solve the equation h=DX by way of a sparsest solution to thereby determine the semantic subspace where the subject exists; and determine which semantic subspace has the most contents of h according to the value of each element in the coefficient vector X, thereby determining which semantic subspace h is most likely to exist.

In an embodiment, the sparsest solution comprises:

solving $x^*=\arg\min\|X\|_1$, wherein X satisfies $\|DX-h\|_2 \leq \varepsilon$, and wherein $\|\bullet\|_1$ is L1 paradigm, and $\|\bullet\|_2$ is L2 paradigm, wherein the cases corresponding to non-zero dimensions in the obtained solution $x^*$ constitute the semantic subspace that h is in.

In an embodiment, the first analyzer is further configured to:

calculate the semantic consistency between the semantic subspace that h is in and the semantic subspace $D_i$ by the following equations:

$$C_i = \frac{\|h_i\|_2^2}{\sum_j \|h_j\|_2^2 + \|\eta\|_2^2} (i=1, 2, \ldots, M)$$

$$C_\eta = \frac{\|\eta\|_2^2}{\sum_j \|h_j\|_2^2 + \|\eta\|_2^2},$$

wherein $h=h_1+h_2+\ldots+h_M+\eta$, $h_i=D\delta_i(X)$, $\eta$ is an error, $\delta_i(X)$ represents a column vector obtained by multiplying the elements of the coefficient vector X belonging to the dimensions of the semantic subspace $D_i$ by 1 and multiplying those belonging to the rest dimensions by 0.

In an embodiment, the device further comprises:

a first outputting unit configured to output the maximum value of $C_1, C_2, \ldots, C_M, c_\eta$ as the probability $P_1$ of the subject being in the semantic subspace that the subject belongs to.

In an embodiment, the medical data analysis device further comprises:

an accessor configured to access the medical knowledge graph to obtain the portion of the medical knowledge graph in relation to the subject, the portion of the medical knowledge graph comprising a plurality of nodes $V=\{v_1, v_2, \ldots, v_N\}$ and an initial evidence score set $p_0=[p_{0,1}, p_{0,2}, \ldots, p_{0,N}]$ for said plurality of nodes, wherein N indicates the number of said plurality of nodes, $$\sum_{i=1}^{N} p_{0,i} = 1,$$

each node $v_i$ represents one physical parameter or one relevant category, i is an index for indexing the node, and $p_{0,i}$ represents the initial evidence score of the node $v_i$;

wherein the second analyzer is configured to determine the final evidence score set p for said plurality of nodes based on the evidence transference score of the physical parameter of the subject on the portion of the medical knowledge graph; and wherein the medical data analysis device further comprise a determiner configured to obtain the probability $P_2$ of the subject being in the node that the subject belongs to based on the final evidence score of each node in the final evidence score set p.

In an embodiment, the second analyzer further comprises:

a calculator configured to perform iterative computation by the following equation to determine the final evidence score set p for said plurality of nodes:

$$p_t=(1-d) \times p_0 + d \times p_{t-1} \times W,$$

wherein d is a damping coefficient, $0<d<1$;

$$W = \begin{bmatrix} l_{11} & l_{12} & \ldots & l_{1N} \\ l_{21} & l_{22} & \ldots & l_{2N} \\ \vdots & \vdots & \ldots & \vdots \\ l_{N1} & l_{N2} & \ldots & l_{NN} \end{bmatrix}, l_{ij} = \frac{w_{i,j}}{\sum_{k=1}^{N} w_{i,k}},$$

$w_{i,j}$ represents the weight of an edge $e_{i,j}$ connecting the nodes $v_i, v_j$ in V, $p_{t-1}$ and $p_t$ represent an evidence score set for said plurality of nodes before t iterative computation and that after t iterative computation respectively, the final evidence score set p is determined as $p_t$ after the iterative computation is terminated.

In an embodiment, the condition for terminating the iterative computation is that $p_t$ does not change any longer or reaches the predetermined maximum number of iterations in the iterative computation.

In an embodiment, the second analyzer further comprises:

a calculator configured to determine the final evidence score set p for said plurality of nodes by the following equation:

$$p=(1-d) \times p_0 \times (I-d \times W)^{-1},$$

wherein d is a damping coefficient, $0<d<1$; I is an N×N unit matrix, $$W = \begin{bmatrix} l_{11} & l_{12} & \ldots & l_{1N} \\ l_{21} & l_{22} & \ldots & l_{2N} \\ \vdots & \vdots & \ldots & \vdots \\ l_{N1} & l_{N2} & \ldots & l_{NN} \end{bmatrix}, l_{ij} = \frac{w_{i,j}}{\sum_{k=1}^{N} w_{i,k}},$$

$w_{i,j}$ represents the weight of an edge $e_{i,j}$ connecting the nodes $v_i, v_j$ in V.

In an embodiment, the determiner is further configured to:

determine the probability of falling into each category node by calculating the percentage of the final score of each category node in V in the sum of the final scores of all category nodes in V; and output the maximum probability in the probability as the probability $P_2$ of falling into the category node the subject belongs to.

According to another aspect, there is provided a medical data analysis device, comprising:

a memory configured to store a computer executable instruction; and a processor coupled to the memory, which is configured to execute the computer executable instruction so that the processor can carry out any method as stated above.

According to another aspect, there is provided a computer-readable storage medium, in which a computer readable instruction is stored to enable a computing device to carry out any method as stated above when being executed by the computing device.

BRIEF DESCRIPTION OF DRAWINGS

To explain the technical solutions of the embodiments of the present disclosure more clearly, the drawings used for describing the embodiments will be briefly illustrated. It shall be appreciated that the following drawings are only related to some embodiments. Without making inventive labor, those ordinarily skilled in the art can also obtain other drawings according to these drawings, and the other drawings are within the scope of the present invention.

DETAILED DESCRIPTION

The technical solutions of the embodiments in the present disclosure will be described clearly and completely with reference to the drawings so as to enable those skilled in the art to understand the objects, technical solutions and advantages of some embodiments more clearly. It is obvious that the embodiments described herein are merely a part, not the whole, of the embodiments of the present invention. On the basis of the embodiments in the present disclosure, those ordinarily skilled in the art can obtain other embodiments. All the obtained other embodiments fall within the scope of the present invention. It needs to be pointed out that although the present disclosure makes explanation using medical big data and a medical knowledge graph as an example, those skilled in the art know that the present invention is also applicable to analyze other types of big data and knowledge graph, in such a way to determine which semantic subspace or type in big data or which node or category in the knowledge graph a certain object belongs to. Additionally, it also needs to be noted that, as indicated above, the present invention is not limited to the medical field, so the solutions of all the methods provided by the present disclosure are not methods directly used for disease diagnosis and treatment.

The relevant technique for forecasting diseases based on medical data is to extract features from data, such as detection indexes like blood pressure or blood sugar levels, train a forecast model (such as a logistic regression model) through machine learning, and finally use the model for forecast. This approach, however, has two defects: 1) it is required to set up a model for each disease, and every model shall be used for forecast when a patient goes to see a doctor, which is less efficient; and 2) different detection indexes are required for forecast of different diseases, so the patients may need to take some unnecessary detections, which increases medical costs. Meanwhile, this approach usually uses detection indexes as features, and fails to take full advantage of other useful information like symptoms in the patients' words.

To solve or alleviate at least one defect in the related art, it is desired to provide a new method and device for data forecast and analysis.

Figure 1:
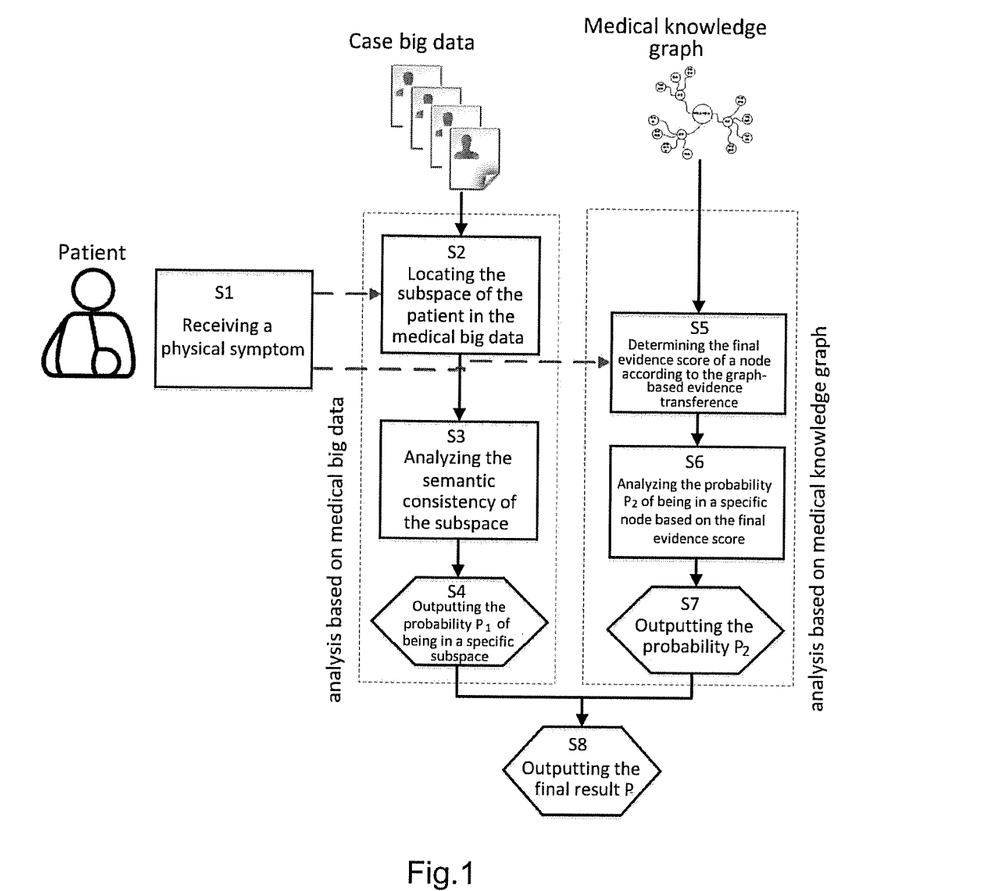
FIG. 1 is a flow chart showing a data analysis method based on medical big data and a medical knowledge graph according to an embodiment.

FIG. 1 is a flow chart showing a data analysis method based on medical big data and a medical knowledge graph according to an embodiment. It should be pointed out that the medical big data herein are merely used as an example, and the present invention is not limited to medical or case-related big data, and may also be applied to other data sets comprising a plurality of semantic subspaces, including, but not limited to, other types of big data. As shown in FIG. 1, the embodiment comprehensively utilizes implicit knowledge in medical big data and explicit knowledge in the medical knowledge graph for disease analysis, to be specific, the method comprises three parts: analysis based on medical big data (the part in the dotted frame in the middle of FIG. 1), analysis based on medical knowledge graph (the part in the dotted frame in the right side of FIG. 1) and output by synthesizing the information of the previous two parts (the step S8 in FIG. 1: final result output). It shall be pointed out that although the embodiment shown in FIG. 1 comprises all the three parts, those skilled in the art can understand that the two parts, namely analysis based on medical big data and analysis based on medical knowledge graph, can be implemented separately as independent technical solutions.

The principle and implementations of the three parts will be described in detail with reference to FIG. 1.

Analysis Based on Medical Big Data

This section will detailedly introduce the basic ideas and implementation of an analysis module based on medical big data. The basic ideas of the module are that patients having similar symptoms may suffer from the same disease; and patients suffering from the same disease are likely to show similar features. This complies with the situations in the real world, for example, a rare disease—"superior semicircular canal dehiscence (SSCD) syndrome"—was first reported by Lloyd Minor, Dean of the Stanford University School of Medicine, and colleagues in 1998. Patients suffering from this disease may have symptoms like getting dizzy and being supersensitive to voice. This should have been an ordinary academic discovery; however, the cause of the disease has not been found for many years in the world, or the patients undergoing clinical trials at other departments in hospitals finally have their diseases confirmed and treated by searching relevant symptom information.

According to some embodiments of the present invention, the part "analysis based on medical big data" comprises four steps: S1, receiving physical symptoms of a patient or a subject; S2, searching the semantic subspace of the patient or object in the medical big data; S3, analyzing the semantic consistency of the semantic subspace; and S4, outputting an analysis result $P_1$ based on the medical big data, namely, the probability $P_1$ of the patient or object being in a particular semantic subspace (the semantic subspace to which the patient or object belongs).

First, physical symptoms of a patient are received in the step S1. The primary function of this step is to collect self-described symptoms of a patient during a visit to the doctor, such as dizziness or headache. It shall be pointed out that the self-described physical symptoms herein are merely exemplary, and the present invention is not limited to those self-described physical symptoms, but can also be applied to physical symptoms obtained by such means as inspection, olfaction, inquiry and pulse-taking. In addition, the present invention may also be applied to other physical parameters, including, but not limited to, physical parameters obtained without body examination or through very simple body examination.

Then, the method goes on to the step S2 for searching the semantic subspace of the patient in the medical big data. The primary function of this step is to look for the semantic subspace of the patient in the medical big data according to the collected symptoms. Since this embodiment analyzes the disease based on medical big data, a large number of cases are required, such as confirmed cases in hospitals over the years, which correspond to the "case-related big data" module in FIG. 1.

The present disclosures uses the symbol $D=[D_1, D_2, \ldots, D_M]$ to represent the collection of the cases.

Suppose it comprises M kinds of diseases, $D_i(1 \leq i \leq M)$ means the i-th disease, wherein $D_1$ may be expressed as $D_1=[D_{i,1}, D_{i,2}, \ldots, D_{i,K}]$, which means that the i-th disease comprises K cases, and $D_{i,j}(1 \leq i \leq M, 1 \leq j \leq K)$ refers to the j-th case suffering from the i-th disease. Each case consists of a series of corresponding feature vectors (e.g., symptom), so the matrix D constitutes a semantic space of a confirmed case, and $D_i(1 \leq i \leq M)$ constitutes a semantic subspace within the semantic space. It shall be pointed out that although medical big data are used as an example for explanation, the present invention can also analyze other types of big data to thereby determine which semantic subspace or category in the big data a certain object exists. In a general example, big data may comprise a plurality of semantic subspaces indicative of a plurality of categories respectively with each category having corresponding cases that are each characterized by a plurality of features. Thus, in the embodiment provided by the present disclosure, the inputted features of a subject can be used to locate or search the semantic subspace where the subject exists, the principle of which is completely identical with that of locating the semantic subspace where the patient exists. In a more general example, the present invention is not limited to big data, and may be applied to a data set including a plurality of semantic subspaces.

As mentioned above, each case consists of a series of corresponding feature vectors, so $D_{i,j}(1 \leq i \leq M, 1 \leq j \leq K)$ can be used to represent the j-th case suffering from the i-th disease. So is it for new patient, who also consists of a series of corresponding feature vectors and can be represented by the vector h. For a new patient h, suppose he/she has a disease $D_i$, then according to the basic idea of the module that patients suffering from the same disease are likely to show similar symptoms, the new patient h can be represented by a linear combination of cases in $D_i$.

$$h = \alpha_{i,1} \times D_{i,1} + \alpha_{i,2} \times D_{i,2} + \ldots + \alpha_{i,K} \times D_{i,K}$$

wherein, $\alpha_{i,j}(1 \leq j \leq K)$ is a relevant coefficient. For instance, as for the disease "hypertension", the symptoms in case 1 are "dizziness, nausea, palpitation and shortness of breath", the symptoms in case 2 are "palpitation and shortness of breath, tinnitus, numbness in limbs", the symptoms in case 3 are "dizziness, nausea, tinnitus, palpitation and shortness of breath" and the symptoms of the new patient are "palpitation and shortness of breath, numbness in limbs", so "the new patient=case 1+case 2−case 3".

For a more general explanation, let the set S be all the symptoms in the set D of collected cases, and |S| be the number of symptoms in the set S, we use a column vector of |S| dimensions to represent a case. For instance, as for cases 1, 2 and 3, S={dizziness, nausea, palpitation and shortness of breath, tinnitus, numbness in limbs}$^T$, S comprises five symptoms. We set dizziness to be the first dimension of the vector, and numbness in limbs to be the fifth dimension by analogue, so different symptoms in the cases correspond to different dimensions of the vector. Let 1 be the dimension corresponding to the symptoms that the patient has, and 0 be the dimension corresponding to the symptoms that the patient does not have. Thus, case $1=[1,1,1,0,0]^T$, case $2=[0,0,1,1,1]^T$, case $3=[1,1,1,1,0]^T$, wherein the superscript T means the transpose of a matrix. The new patient $h=[0,0,1,0,1]^T=[1,1,1,0,0]^T+[0,0,1,1,1]^T-[1,1,1,1,0]^T$. That is to say, "the new patient=case 1+case 2−case 3". Suppose the disease "hypertension" corresponds to the i-th disease, $D_{i,1}=[1,1,1,0,0]^T$; $D_{i,2}=[0,0,1,1,1]^T$; $D_{i,3}=[1,1,1,1,0]^T$; $h=D_{i,1}+D_{i,2}-D_{i,3}$. In this example, the case vector is set to be a column vector. However, those skilled in the art can understand that the case vector may also be a line vector, and accordingly, the case set and dimensions of other vectors shall be transposed.

For the sake of brevity and convenience, the above expression can also be represented by a matrix. Suppose $D_i=[D_{i,1}, D_{i,2}, \ldots, D_{i,K}]$, $x_i [\alpha_{i,1}, \alpha_{i,2}, \ldots, \alpha_{i,K}]^T$, wherein the superscript T means the transpose of a matrix, then $$h = D_i x_i$$

Figure 2:
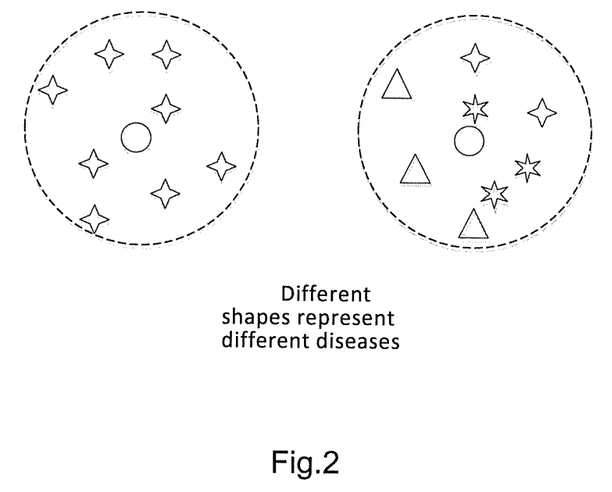
FIG. 2 is a schematic view exemplarily illustrating a plurality of semantic subspaces in a big data space.

Through the above discussion, it can be seen that each disease can be represented by a semantic subspace consisting of known cases included therein, and a case suffering from the disease can consist of linear combinations of a base of a corresponding semantic subspace. FIG. 2 is a schematic view exemplarily illustrating a plurality of semantic subspaces in a big data space.

On the basis of the above discussion, if a case set D is given, the disease can be determined by searching the semantic subspace of the patient h in D. Suppose $D=[D_1, D_2, \ldots, D_M]$, the semantic subspace of the patient h can be obtained by the following equation (1):

$$h = DX \quad (1)$$

wherein, $D=[D_1, D_2, \ldots, D_M]=[D_{1,1}, D_{1,2}, \ldots, D_{i,1}, D_{i,2}, \ldots, D_{M,K}]$ is a matrix, which comprises all the diseases $D_i(1 \leq i \leq M)$ in D, and wherein each element $D_{i,j}(1 \leq i \leq M, 1 \leq j \leq K)$ corresponds to one case in D, namely, the j-th case suffering from the i-th disease, and each case is also a column vector.

Wherein, X is a column vector, $X=[x_1^T, x_2^T, \ldots, x_i^T, \ldots, x_M^T]^T$, and the dimension thereof is not M, but the number of cases in D, namely, the dimension is the same as $[D_{1,1}, D_{1,2}, \ldots, D_{i,1}, D_{i,2}, \ldots, D_{M,K}]$. For instance, suppose D comprises two diseases with disease 1 comprising a cases and disease 2 comprising b cases, then the dimension of X is a+b.

However, since the space of D is very large, there are many Xs that can satisfy the equation (1), namely there are multiple semantic subspaces in which h can be reconstructed. To solve this problem, the present invention adopts a sparsest solution (to reconstruct h with the least cases). The advantage of using the sparsest solution is to reduce the impact of "noisy data" to enable the model to have a good robustness. To be specific, $$x^* = \mathrm{argmin} \|X\|_1$$

which satisfies $$\|DX - h\|_2 \leq \varepsilon \quad (2)$$

wherein, $\|\bullet\|_1$ is L1 paradigm used for calculating the sum of the absolute values of all the elements, $\|\bullet\|_2$ is L2 paradigm used for calculating the sum of squares of all elements. $\varepsilon$ is a predetermined parameter. $X=[\alpha_{1,1}, \alpha_{1,2}, \ldots, \alpha_{i,K}, \ldots]^T$ is the coefficient to be solved. The cases corresponding to non-zero dimensions in x* solved by the equation (2) constitute the semantic subspace that h is in. Thus, it is required to have a column vector X that enables the sum of the absolute values of all elements in the determined X to be the minimum, and each element in the vector obtained by matrix multiplication DX is very close to the patient's symptoms, wherein the specific value of is solved by the equation (2) using stochastic gradient descent method.

The above example, namely a new patient $h=[0,0,1,0,1]^T=[1,1,1,0,0]^T+[0,0,1,1,1]^T-[1,1,1,1,0]^T$, is an ideal example. In reality, due to the limitation of calculation accuracy, it might occur that $\alpha_{i,j}$ is not the best solution. For instance, in this example, suppose $\alpha_{1,1}=0.8$, then 0.8*[1,1, $1,0,0]^T+[0,0,1,1,1]^T-[1,1,1,1,0]^T=[0.2,0.2,0.8,0,1]$. Thus, $Dx-h=[0.2,0.2,0.8,0,1]^T-[0,0,1,0,1]^T=[0.2,0.2,-0.2,0,0]^T$, and $\|DX-h\|_2=0.12$. If we let $\varepsilon=0.2$, then $\|DX-h\|_2 \le \varepsilon$ still holds. Introduction of $\varepsilon$ is just for reducing the impact of "noises". In the event that $\alpha_{i,j}$ are not equal, it is still possible to compute. When solving through the equation (2), $\alpha_{i,j}$ do not need to be equal because they are just a weight of a vector.

Then, the method goes on to the step S3 to perform an analysis on semantic consistency of semantic subspace. The primary function of this step is to analyze the probability of h being in a particular semantic subspace (namely, the semantic subspace to which h belongs) by analyzing the semantic consistency of the semantic subspace that h is in. Let $\delta_i(X)$ denote a column vector obtained by multiplying the elements of the coefficient vector X belonging to the dimensions of the semantic subspace $D_i$ by 1 and multiplying those belonging to the rest dimensions by 0, and hence the dimension thereof is the number of all the cases in D, namely, the dimension thereof is identical with $[D_{1,1}, D_{1,2}, \ldots, D_{i,1}, D_{i,2}, \ldots, D_{M,K}]$. The semantic element in the vector h that corresponds to the semantic subspace $D_i$ is $h_i=D\delta_i(x)$, then h can be expressed as $h=h_1+h_2+\ldots+h_M+\eta$, wherein $\eta$ is the error. Based on the above expression, the present invention defines the semantic consistency between the semantic subspace that h is in and the semantic subspace $D_i$ as follows:

$$C_i = \frac{\|h_i\|_2^2}{\sum_j \|h_j\|_2^2 + \|\eta\|_2^2} (i = 1, 2, \ldots, M) \quad (3)$$

$$C_\eta = \frac{\|\eta\|_2^2}{\sum_j \|h_j\|_2^2 + \|\eta\|_2^2}$$

Wherein, $\|\cdot\|_2$ is the square of L2 paradigm.

After the semantic consistency of the semantic subspace is analyzed in the step S3, the result of analysis based on medical big data is outputted in the step S4. That is to say, the maximum value of $C_1, C_2, \ldots, C_M, c_\eta$ is outputted as the probability $P_1$ of the patient being in the semantic subspace corresponding to the maximum value. Meanwhile, the semantic subspace or category corresponding to the maximum value is finally determined as the semantic subspace or category where the patient exists.

The primary function of the step S4 is to output the result of analysis based on medical big data. Let $C=[C_1, C_2, \ldots, C_M, C_\eta]$, it can be seen from the definition of the equation (3) that $C_1+C_2+\ldots+C_M+C_\eta=1$, $C_i$ reflects the possibility of h being in the semantic subspace $D_i$, namely, it corresponds to the probability $P_1$ in FIG. 1, wherein $C_\eta$ reflects the possibility or probability of h being not in any one of the semantic subspaces $D_1$-$D_M$. It is because the larger $C_i$ is, the more cases that fall into the semantic subspace $D_i$ in the vector constituting h, that is to say, the larger the part of h in the semantic subspace $D_i$ is, the more likely it belongs to the semantic subspace $D_i$. For instance, in FIG. 2, suppose the known case space has three semantic subspaces respectively corresponding to different shapes: a four-pointed star node, a triangle node and a six-pointed star node, and respectively corresponding to the first three dimensions of C, the error of the last dimension is $C_\eta$. A round node refers to a new patient. Two circles in FIG. 2 respectively denote two linear combination types indicative of new patients. The first type merely uses a semantic subspace represented by a four-pointed star node to denote a new patient, and the second type uses all the three semantic subspaces to denote a new patient. As can be clearly seen, $C=[1,0,0,0]$ in the left view, namely, the patient may be in the semantic subspace represented by the four-pointed star; and $C=[0.25, 0.375, 0.375, 0]$ in the right view, so it is very hard to analyze which semantic subspace or category the patient belongs to.

Some embodiments of the present disclosure analyze the patient's conditions based on medical big data. The solution uses the patient's physical symptoms as features, locate the patient's semantic subspace in the medical big data according to the patient's symptoms, and analyze the patient's disease conditions based on the semantic consistency of the semantic subspace. In comparison with the prior art, the solution does not need to set up one model for each disease and is highly efficient in prediction. Analysis based on the patient's physiological phenomena (symptoms) renders it possible to analyze the patient's conditions according to symptoms in the first time and then conduct targeted examinations on the patient, thereby decreasing costs and increasing efficiency.

Analysis Based on Medical Knowledge Graph

Figure 3:
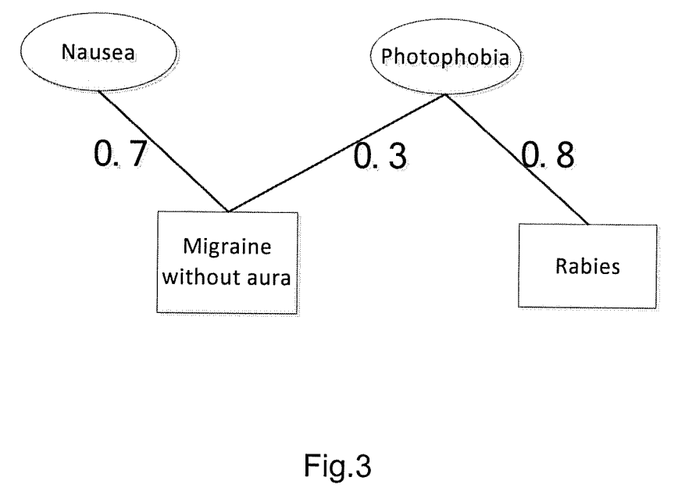
FIG. 3 illustrates an example of graph-based evidence propagation in a medical knowledge graph.

The second part, namely analysis based on medical knowledge graph, of the flow chart shown in FIG. 1 will be described. This section will introduce the basic idea and implementation of an analysis module based on medical knowledge graph. FIG. 3 illustrates an example of graph-based evidence propagation in a medical knowledge graph. In the medical knowledge graph, a node denotes a disease or symptom (in a more general example, a category and feature), and the edge between nodes denotes the semantic relevance between nodes. The basic idea of analysis based on the medical knowledge graph is that propagation of symptom (or disease) gives higher evidence scores to the disease (or symptom) of higher semantic relevance than the one of lower semantic relevance. For instance, as shown in FIG. 3, suppose the weighted score of "migraine without aura" is 1, it can propagate 0.7 evidence score to the symptom "nausea", and 0.3 evidence score to the symptom "photophobia". To explain it in plain language, there is a 70% probability that the patient suffering from migraine without aura has nausea and a 30% probability that the patient has photophobia, that is to say, nausea occurs in the patient suffering from migraine without aura more frequently than photophobia. The probability that the patient with "rabies" has photophobia is 80%.

It should be pointed out that the present invention is also applicable to other knowledge graphs that are structurally similar to the medical knowledge graph for use in analyzing and determining the node or category of a certain object, the principle of which is completely identical with that of the solution based on the medical knowledge graph.

The graph-based evidence propagation method will be introduced in detail with reference to the flow chart shown in FIG. 1.

In the step S5, the method carries out the graph-based evidence propagation, i.e., analyzing the probability $P_2$ of a patient being at a disease node based on the evidence propagation score on the medical knowledge graph. The step functions to analyze the patient's situations according to the patient's symptoms and in combination with explicit medical knowledge in the medical knowledge graph. To be specific, an initial evidence score of a symptom is given, and then the evidence score is propagated in the medical knowledge graph until the evidence scores of all the nodes will never vary or vary a little based on the basic idea that "propagation of symptom (or disease) gives higher evidence scores to the disease (or symptom) of higher semantic relevance than the one of lower semantic relevance".

It should be pointed out that the value of the initial evidence score does not matter, because the final score has nothing to do with the initial value according to the Markov Chain Convergence Theory. However, in engineering, a "good" initial value is helpful for convergence. For example, it takes 10,000 times to converge a "bad" initial value to the final result, but it may only need 1,000 times to converge a "good" initial value to the final result. Of course, there is no difference in the result finally achieved. Generally speaking, a "good" initial value is set based on empirical knowledge. For instance, in virtue of empirical knowledge, a greater weight can be set for the initial evidence score with more prominent symptoms. If we have no idea of which one is more prominent, which means there is no empirical knowledge, the common way is to set the same weight for each evidence score according to the principle Ockham's Razor, at the time of which the entropy is the largest.

In an embodiment, suppose $V=\{v_1, v_2, \ldots, v_N\}$ denotes the collection of vertexes or nodes in the medical knowledge graph, $E=\{\ldots, e_{i,j}, \ldots\}$ denotes the collection of edges between the nodes, wherein N indicates the number of the nodes in the medical knowledge graph, represents the edge between the nodes $v_i$ and $v_j$, and wherein i and j are both indexes for indexing the nodes, $1 \leq i \leq N$, $1 \leq j \leq N$, $i \neq j$ is the set of weights of all edges, wherein $w_{i,j}$ is the weight of the edge $e_{i,j}$. Let the initial evidence score set for said nodes in the medical knowledge be $p_0[p_{0,1}, p_{0,2}, \ldots, p_{0,N}]$, wherein $$\sum_{i=1}^{N} p_{0,i} = 1,$$

and $p_{0,i}$ denotes the initial evidence score of the node $v_i$. For instance, in FIG. 3, suppose the patient has the symptoms of "nausea" and "photophobia", the initial evidence score set can be set as $p_0$["nausea", "photophobia", "migraine without aura", "rabies" ]=[0.5, 0.5, 0, 0], that is, where there is no empirical knowledge, the distribution that satisfies the condition and has the largest entropy can be used as the initial evidence score set.

Let $p_t=[p_{t,1}, p_{t,2}, \ldots, p_{t,N}]$ be the evidence score set for said nodes in the medical knowledge after t iterations of evidence propagation. The evidence propagation herein is the score passed from one vertex to another. For instance, the score of a vertex is 1, and the weight of the edge between the vertex and other vertex is 0.6, then the evidence score passed from the vertex A to the other vertex is 1*0.6=0.6. Based on the basic idea that "propagation of symptom (or disease) gives higher evidence scores to the disease (or symptom) of higher semantic relevance than the one of lower II) semantic relevance", the evidence score set for said nodes in the medical knowledge after t+1 iterations is $$p_{t+1,i} = (1-d) \times p_{0,i} + d \times \left( \sum_{j \in M(i)} \frac{w_{j,i}}{\sum_k w_{j,k}} \times p_{t,j} \right) \quad (4)$$

Wherein, d is a damping coefficient (0<d<1); and M(i) denotes the set of nodes connected with the node $v_i$. By taking the example in FIG. 3 for example, suppose the initial evidence score set for said nodes in the medical knowledge is $p_0$ ["nausea", "photophobia", "migraine without aura", "rabies" ]=[0.5, 0.5, 0, 0], and the edge weights are those shown in FIG. 3, then after one iteration, the evidence score of "nausea" is (1−d)×0.5+0×0.7=0.1 (suppose d=0.8), the evidence score of "photophobia" is 0.2×0.5+0×0.8=0.1, the evidence score of "migraine without aura" is $$0.8 \times 0.5 \times \frac{0.7}{0.7} + 0.8 \times 0.5 \times \frac{3}{11} + 0.2 \times 0 = 0.51,$$

and similarly the score of "rabies" can be calculated, $$0.8 \times 0.5 \times \frac{8}{11} + 0.2 \times 0 = 0.29.$$

Then, the equation (4) is solved via iteration until a termination condition is met, i.e., $p_t$ does not change any longer or reaches the predetermined maximum number of iterations. The predetermined maximum number of iterations is set in engineering to prevent the computation from taking too much time. Although, according to the Markov Chain Convergence Theory, the propagation process of evidence score will finally converge, it cannot be ensured, in principle, how many cycles (or how long) it needs for convergence. In order to avoid that a long time is spent on convergence, the maximum number of iterations, such as, 1 million cycles, are generally set. If the convergence is not achieved, it is very close to the convergence result, and there is no need to further waste a large amount of time to obtain the convergence result. Thus, the maximum number of iterations is a manifestation of reconciliation and balance between time efficiency and result precision.

For the sake of brevity and enhanced efficiency, the equation (4) may be changed into a form represented by a matrix as follows:

$$p_{t+1} = (1-d) \times p_0 + d \times p_t \times W \quad (5)$$

$$\text{wherein, } W = \begin{bmatrix} l_{11} & l_{12} & \ldots & l_{1N} \\ l_{21} & l_{22} & \ldots & l_{2N} \\ M & M & \ldots & M \\ l_{N1} & l_{N2} & \ldots & l_{NN} \end{bmatrix}$$

$$l_{ij} = \frac{w_{i,j}}{\sum_{k=1}^{N} w_{i,k}}$$

According to the Markov theory, $$\lim_{t \to \infty} p_t$$

certainly exists. The limit is taken on both sides of the equation (5):

$$\lim_{t \to \infty} p_{t+1} = \quad (6)$$

$$\lim_{t \to \infty} \{(1-d) \times p_0 + d \times p_t \times W\} \Rightarrow p = (1-d) \times p_0 + d \times p \times W,$$

$$\text{wherein } p = \lim_{t \to \infty} p_t \Rightarrow p = (1-d) \times p_0 \times (I - d \times W)^{-1}$$

Wherein I is an N×N unit matrix, and the value of $p_i$ is the final evidence score of the node $v_i$. It can be seen that according to the formulation (6), the final evidence score set for said nodes in the medical knowledge can be directly calculated. For instance, the final evidence score set, p["nausea", "photophobia", "migraine without aura" and "rabies"]=[0.25, 0.30, 0.27, 0.18], for the nodes in FIG. 3 can be directly obtained. The higher the final evidence score of a disease node is, the more likely the patient is in the node. Thus, the scores of the disease nodes can be normalized to obtain the probability of the patient being in the node, which corresponds to $P_2$ in FIG. 1. For instance, in the example in FIG. 3, the probability of the patient being at the node of "migraine without aura" is $$\frac{0.27}{0.27+0.18} = 60\%,$$

and the probability of the patient being at the node of "rabies" is $$\frac{0.18}{0.27+0.18} = 40\%.$$

Some embodiments of the present disclosure propose disease analysis by utilizing a medical knowledge graph, and the embodiment analyzes the patient's conditions by transferring relevant evidence by the symptoms in the medical knowledge graph, wherein the knowledge graph is established based on medical knowledge. The embodiment can make use of the explicit knowledge or information in the knowledge graph for disease analysis, and analyze the patient's conditions according to the symptoms in the first time so that the patient can undergo examination purposefully, thereby reducing costs and improving efficiency.

Figure 4:
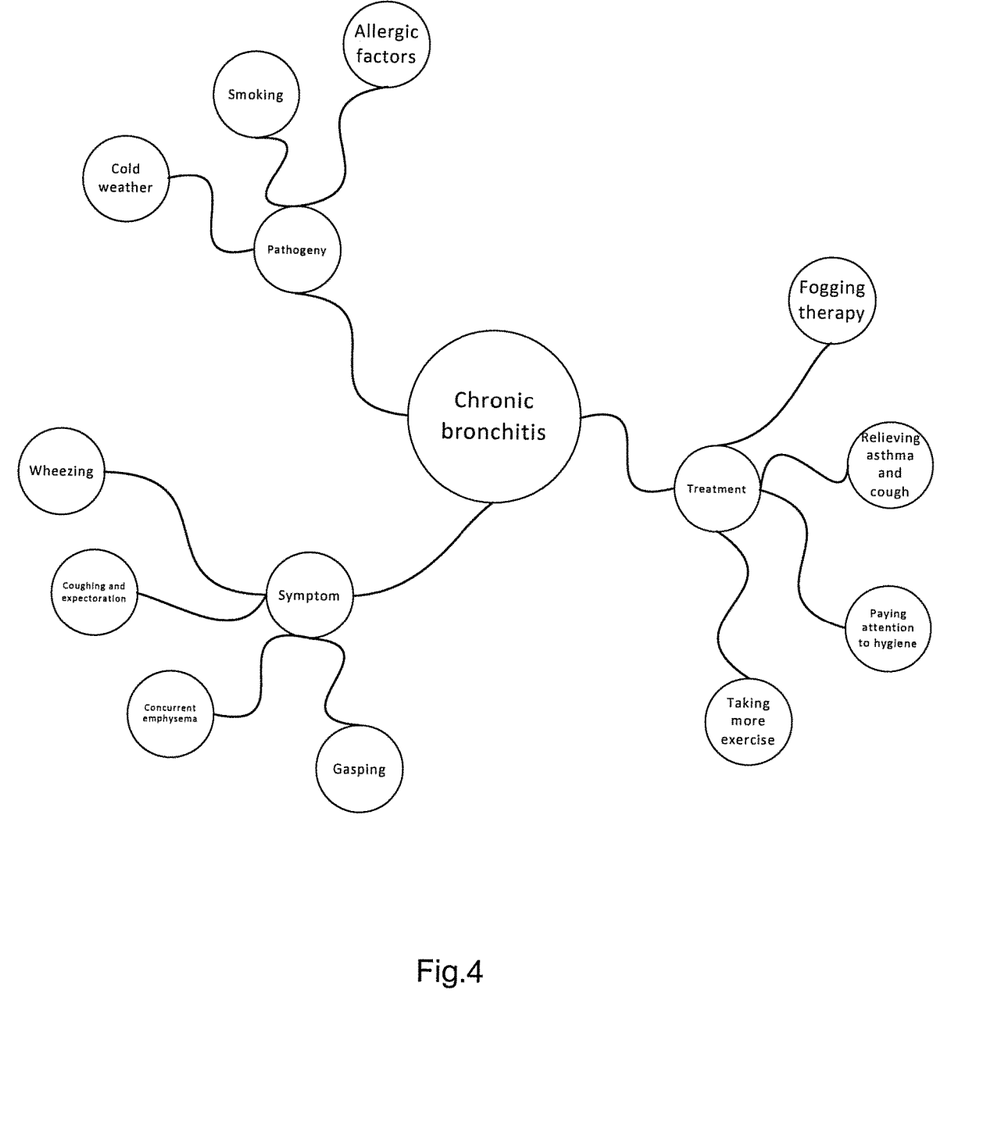
FIG. 4 is a schematic view showing a simplified example of the medical knowledge graph.

FIG. 4 is a schematic view showing a simplified example of the medical knowledge graph, wherein the big circle in the center refers to a category in the knowledge graph, and a disease in the present example, and the nodes directly connected with the big circle refer to the relationships between the category and other features, for example, it may be cause of disease, symptoms or treatment in the present example. The outmost circle refers to corresponding features, which may be symptoms, cause of disease and treatment. For the sake of brevity, the weight of the edge is omitted in FIG. 4.

Then, the method goes on to the step S7 for outputting the probability $P_2$ of a patient being at a disease node or belonging to a category obtained through analysis based on the medical knowledge graph.

In the end, the method goes on to the step S8 for outputting the final result, that is to say, determining the probability of the patient belonging to a category based on $P_1$ obtained in the step $S_4$ and $P_2$ obtained in the step $S_7$. The function of this step is to provide the final analytical result by synthesizing the analysis based on the medical data and the analysis based on the medical knowledge graph. To be specific, the scores of the two are synthesized by a linear weighted method. Specifically, the probability of the patient belonging to a category can be calculated or determined by the following equation:

$$P=\alpha \times P_1 + (1-\alpha) \times P_2$$

wherein α is a reconciling parameter, 0≤α≤1, which is used to adjust the proportion of the two analytical methods. If the medical big data are sufficient and of high quality, and the accuracy of analysis based on the medical data is high, a can be raised (such as, α=0.7); contrarily, if the medical big data are insufficient or of low quality, and the accuracy of analysis based on the medical big data is not high, analysis shall be conducted by making full use of the medical knowledge on the medical knowledge graph, and a can be lowered (such as, α=0.2).

Some embodiments of the present disclosure conduct comprehensive analysis of diseases based on the medical big data and the medical knowledge graph. The embodiment utilizes the physical parameter of a patient as a feature so as to, on the one hand, locate the semantic subspace of the patient in the medical big data according to the symptoms of the patient, and analyze the conditions of the patient according to the semantic consistency of the semantic subspace, and on the other hand, analyze the conditions of the patient by transferring relevant evidence according to the symptoms in the medical knowledge graph. At last, the information in the two aspects shall be synthesized for analysis and then the final conclusion or result can be outputted. In comparison with the previous approach, the embodiment can comprehensively utilize the implicit law, knowledge or information in the large-scale medical big data and the explicit knowledge or information in the knowledge graph for disease analysis, thereby improving the analytical accuracy; meanwhile, analysis can be conducted by making use of the physical phenomena (symptoms) of the patient so as to analyze the patient's conditions according to symptoms in the first time and then conduct targeted examinations on the patient, thereby decreasing costs and increasing efficiency.

Figure 5:
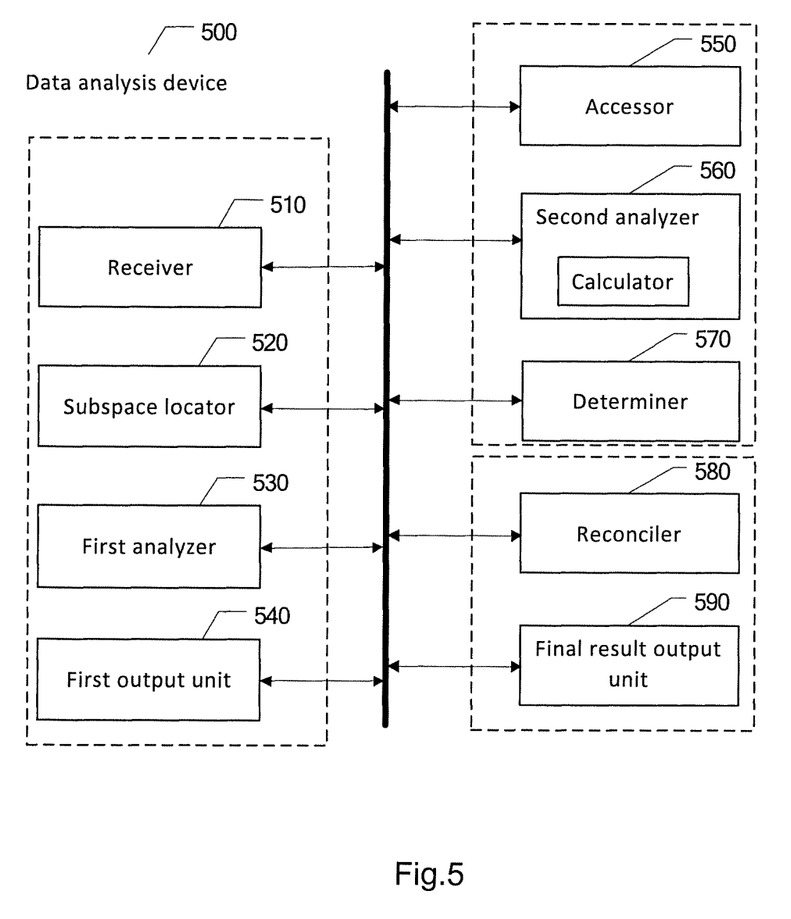
FIG. 5 is a structural schematic view of a data analysis device according to an embodiment.

FIG. 5 is a structural schematic view of a data analysis device according to an embodiment. In the present example, the data analysis device conducts analysis based on the medical big data and the medical knowledge graph. Similar to FIG. 1, the data analysis device 500 in FIG. 5 also comprises three parts, i.e., a big data analysis device (as shown in the left dotted frame), a medical data analysis device (the part in the upper-right dotted frame and the receiver 510) and a reconciling part for reconciling the results outputted from the above-mentioned two parts (as shown in the lower-right dotted frame). Those skilled in the art can understand that the big data analysis device and the medical data analysis device can be implemented separately as independent devices. It shall be additionally noted that the big data analysis device can also be used to analyze other big data so as to determine the semantic subspace or category of a subject in the big data space, and the medical data analysis device can also analyze other types of knowledge graphs that are structurally similar to the medical knowledge graph, thereby determining the node or category of a subject in the knowledge graph.

As shown in FIG. 5, the big data analysis device may comprise a receiver 510, a subspace locator 520, a first analyzer 530 and an optional first output unit 540. The receiver 510 can be configured to receive a physical symptom of a patient and use a vector h to represent the physical symptom. The subspace locator 520 can be configured to locate the semantic subspace of the patient in the medical data by taking the physical symptom as a feature, wherein a matrix D is used to represent a collection of cases in the big data, $D=[D_1, D_2, \ldots, D_M]$, $D_i$ represents an i-th semantic subspace, 1≤i≤M. The step of locating may comprise: solving the equation h=DX, wherein X is a coefficient vector indicative of the distribution of the vector h in each semantic subspace. The first analyzer 530 can be configured to analyze the probability $P_1$ of the patient being in the specific semantic subspace or category (namely, the semantic subspace or category the patient belongs to) by analyzing the semantic consistency of the semantic subspace where the physical symptom vector h exists.

In an embodiment, the subspace locator 520 can be further configured to solve the following equation by way of a sparsest solution to thereby determine the semantic subspace where the patient exists: h=DX. The subspace locator 520 can be further configured to determine which semantic subspace has the most contents of h according to the value of each element in the coefficient vector X, thereby determining which semantic subspace h is most likely to exist.

In an embodiment, the sparsest solution comprises: solving x*=arg min$\|X\|_1$, wherein X satisfies $\|DX-h\|_2 \leq \varepsilon$, and wherein $\|\bullet\|_1$ is L1 paradigm, and $\|\bullet\|_2$ is L2 paradigm. The cases corresponding to non-zero dimensions in the obtained solutions x* constitute the semantic subspace that h is in.

In an embodiment, the first analyzer 530 can be further configured to calculate the semantic consistency between the semantic subspace that h is in and the semantic subspace $D_i$ by the following equations:

$$C_i = \frac{\|h_i\|_2^2}{\sum_j \|h_j\|_2^2 + \|\eta\|_2^2} (i = 1, 2, ..., M)$$

$$C_\eta = \frac{\|\eta\|_2^2}{\sum_j \|h_j\|_2^2 + \|\eta\|_2^2},$$

wherein $h = h_1 + h_2 + \ldots + h_M + \eta$, $h_i = D\delta_i(X)$, $\eta$ is an error, $\delta_i(X)$ represents a column vector obtained by multiplying the elements of the coefficient vector X belonging to the dimensions of the semantic subspace $D_i$ by 1 and multiplying those belonging to the rest dimensions by 0.

In an embodiment, the optional first output unit 540 can be configured to output the maximum value of $C_1, C_2, \ldots, C_M, c_\eta$ as the probability $P_1$ of the patient being in the corresponding semantic subspace or belonging to the corresponding category.

The medical data analysis device may comprise a receiver 510, an accessor 550, a second analyzer 560 and a determiner 570. The accessor 550 can be configured to access the medical knowledge graph to obtain the portion of the medical knowledge graph in relation to the patient, the portion of the medical knowledge graph comprises a plurality of nodes $V = \{v_1, v_2, \ldots, v_N\}$ and an initial evidence score set $p_0 = [p_{0,1}, p_{0,2}, \ldots, p_{0,N}]$ for plurality of nodes, wherein N indicates the number of said plurality of nodes, $$\sum_{i=1}^{N} p_{0,i} = 1,$$

each node $v_i$ represents one symptom or one relevant disease of the patient (one feature or one category in a more general example), i is an index for indexing the node, and $p_{0,i}$ represents the initial evidence score of the node $v_i$. The second analyzer 560 can be configured to determine the final evidence score set p for said plurality of nodes based on the evidence transference score of the physical symptom of the patient on the portion of the medical knowledge graph. The determiner 570 can be configured to analyze the probability $P_2$ of the patient being in the specific node or category (namely, the node or category he/she belongs to) based on the final evidence score of each node in the final evidence score set p. In an embodiment, the second analyzer 550 can further comprise a calculator. The calculator can be configured to perform iterative computation by the following equation to thereby determine the final evidence score set p for said plurality of nodes:

$$p_t = (1-d) \times p_0 + d \times p_{t-1} \times W,$$

wherein d is a damping coefficient, 0<d<1;

$$W = \begin{bmatrix} l_{11} & l_{12} & \cdots & l_{1N} \\ l_{21} & l_{22} & \cdots & l_{2N} \\ \vdots & \vdots & \cdots & \vdots \\ l_{N1} & l_{N2} & \cdots & l_{NN} \end{bmatrix}, l_{ij} = \frac{w_{i,j}}{\sum_{k=1}^{N} w_{i,k}},$$

$w_{i,j}$ represents the weight of an edge $e_{i,j}$ connecting the nodes $v_i$, $v_j$ in V, $p_{t-1}$ and $p_t$ represent an evidence score set for said plurality of nodes before t iterative computation and that after t iterative computation respectively, the final evidence score set p is determined as $p_t$ after the iterative computation is terminated. In an embodiment, the condition for terminating the iterative computation is that $p_t$ does not change any longer or reaches the predetermined maximum number of iterations in the iterative computation.

In another embodiment, the calculator can be configured to determine the final evidence score set p for said plurality of nodes by the following equation:

$$p = (1-d) \times p_0 \times (I - d \times W)^{-1},$$

wherein d is a damping coefficient, 0<d<1; I is an N×N unit matrix, $$W = \begin{bmatrix} l_{11} & l_{12} & \cdots & l_{1N} \\ l_{21} & l_{22} & \cdots & l_{2N} \\ \vdots & \vdots & \cdots & \vdots \\ l_{N1} & l_{N2} & \cdots & l_{NN} \end{bmatrix}, l_{ij} = \frac{w_{i,j}}{\sum_{k=1}^{N} w_{i,k}},$$

$w_{i,j}$ represents the weight of an edge $e_{i,j}$ connecting the nodes $v_i$, $v_j$ in V.

In an embodiment, the determiner 570 can be further configured to: determine the probability of falling into each node by calculating the percentage of the final score of each disease node in V in the sum of the final scores of all disease nodes in V; and output the maximum probability in the probability as the probability $P_2$ of the patient being in the corresponding node or category. Correspondingly, the node and category can be determined as the node or category where the patient belongs to.

The reconciling part may comprise a reconciler 580 and a final result output unit 590. The reconciler 580 can be configured to determine the probability P of the patient being in the specific semantic subspace or node or category (namely, the semantic subspace or node or category the patient belongs to) based on the probability $P_1$ and probability $P_2$: $P = \alpha \times P_1 + (1-\alpha) \times P_2$, wherein $\alpha$ is a reconciling parameter, $0 \leq \alpha \leq 1$. The final result output unit 590 can be configured to output the probability P as the probability of the patient being in the corresponding semantic subspace or node or category.

It shall be pointed out that the data analysis device 500 shown in FIG. 5 can carry out any method step in the method shown in FIG. 1. Since the principle of the present disclosure is identical with that of the analysis method, those skilled in the art can obtain other details of the data analysis device 500 from the description of the method, no more details about the data analysis device 500 and for its components to carry out the method and the steps thereof are given.

Figure 6:
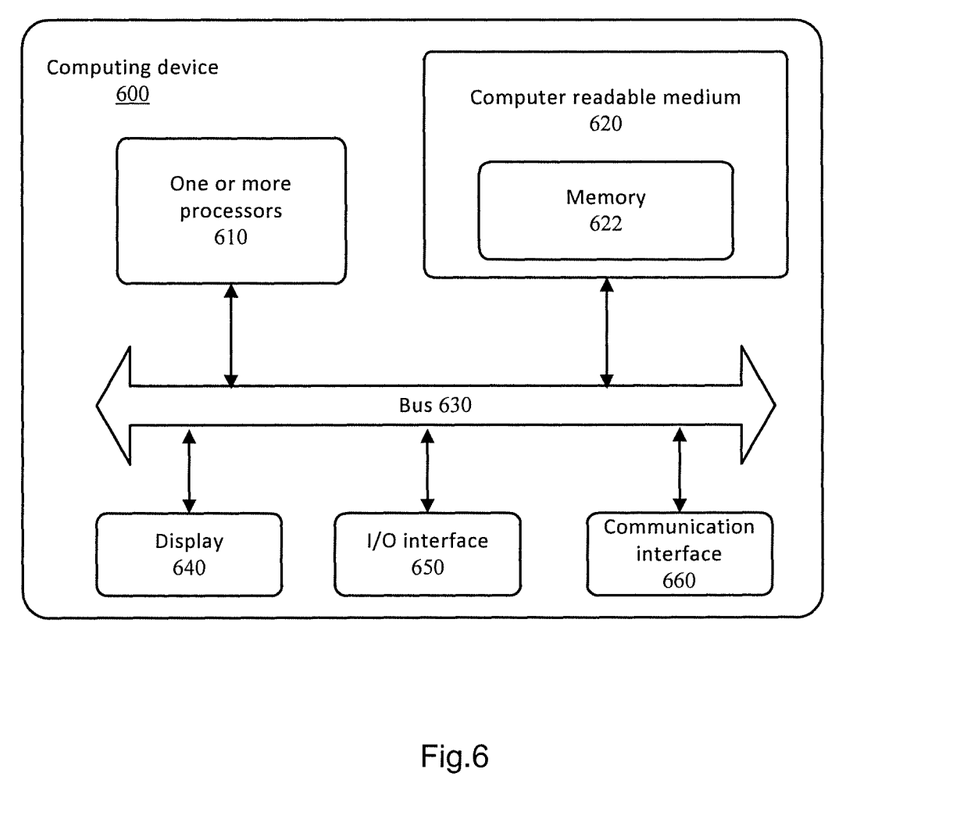
FIG. 6 illustrates an exemplary computing device used for realizing one or more examples.

FIG. 6 illustrates an exemplary computing device 600 used for realizing one or more examples. In particular, the devices according to some embodiments can be realized by the exemplary computing device 600. As shown, the exemplary computing device 600 comprises one or more processors 610 or processing units, one or more computer readable media 620 of one or more memories 622, one or more displays 640 for displaying contents to a user, one or more input/output (I/O) interfaces 650 for use in an input/output (I/O) device, one or more communication interfaces 660 for communicating with other computing device or communication device, and a bus 630 that allows mutual communication between different assemblies and devices.

The computer readable medium 620, the display 640 and/or one or more I/O devices can be included as a part of the computing device 600, or alternatively be coupled to the computing device 600. The bus 630 refers to one or more bus structures of various types, which comprise a storage bus or a storage controller, an peripheral bus, an accelerated graphics port, and a processor or a local bus of any structure that is constructed by various buses. The bus 630 may comprise a wired and/or wireless bus.

There is no limitation to the one or more processors 610 in terms of the materials thereof or the utilized processing mechanism. For instance, the processor can consist of one or more semi-conductors and/or transistors (e.g., electronic integrated circuits (ICs)). Under this background, a processor executable instruction may be an electrically executable instruction. Memory 622 denotes a memory/storage volume associated with one or more computer readable medium. The memory 622 may comprise a volatile medium (such as, a random access memory (RAM)) and/or a non-volatile medium (such as, a read-only memory (ROM), a flash memory, a CD, and a disc, etc.). The memory 622 may comprise a fixed medium (such as, RAM, ROM and a fixed hard disk drive) and a movable medium (such as, a flash memory drive, a movable hard disk drive and a CD).

The one or more input/output interfaces 650 allow the user to input an order and information into the computing device 600, and also allow the information to be presented to the user and/or to other assembly or device using a different input/output device. The examples of the input device comprise a keyboard, a touch-screen display, a cursor control equipment (such as a mouse), a microphone, a scanner and the like. The examples of the output device comprise a display device (such as a monitor or a projector), a loudspeaker, a printer, a network card and the like.

The communication interface 660 allows communication with other computing device or communication device. There is no limitation to the communication interface 660 in terms of the utilized communication technologies. The communication interface 660 may comprise a wired communication interface such as an LAN communication interface and a WAN communication interface, and a wireless communication interface such as an infrared, Wi-Fi or Bluetooth communication interface.

Various technologies herein are described in a general environment of software, hardware (fixed logic circuits) or program modules. Generally speaking, the program module comprises routines, programs, objects, elements, assemblies, data structures and the like for executing a particular task or achieving specific abstract data types. The realization of these modules and technologies can be stored in some type of computer readable medium or transported by means of the computer readable medium. The computer readable medium may comprise various usable agents or media accessible by a computing device.

Specific modules, functions, assemblies and technologies described herein can be realized in software, hardware, firmware and/or combination thereof. The computing device 600 can be configured to execute specific instructions and/or functions corresponding to software and/or hardware module(s) realized on the computer readable medium. The instructions and/or functions can be executed/operated by a manufactured product (such as one or more computing devices 600 and/or processors 610) so as to realize the technologies used herein. Such technologies comprise, but are not limited to, the exemplary process described herein. Hence, the computer readable medium can be configured to store or provide instructions for realizing the above-mentioned different technologies when accessed by one or more devices described herein.

Although the drawings specifically illustrate some embodiments of the present invention, those skilled in the art shall understand that the above specific illustration is merely for explaining the invention, and the invention is not at all limited to the above specific embodiments. Based on the specific depiction and teachings of those embodiments herein, those skilled in the art can make various modifications, additions, replacements and variations to those embodiments without departing from the protection scope of the invention, that is, the modifications, additions, replacements and variations will all be covered by the protection scope of this invention. The protection scope of this invention is defined by the appended claims. Specific features and acts described herein are disclosed as examples capable of realizing the claims.

What needs to be explained is that the above embodiments are only illustrated by way of the individual function modules division. In actual application, the above functions can be allocated to different functional modules as desired. The internal structure of the device can be divided into different functional modules so as to accomplish all or part of the functions as stated above. In addition, function(s) of the above one module can be achieved by a plurality of modules, and functions of the plurality of modules can be integrated into one module.

The present application uses such wordings as "first", "second" and "third". Unless specified in the context, such wordings do not imply any order, but are actually used for the purpose of identification. For instance, the phrases "first analyzer" and "second analyzer" do not necessarily mean the first analyzer is operated or processed earlier than the second analyzer. In fact, these phrases are only used to identify different analyzers.

In the claims, any reference sign in parentheses should not be interpreted as a limitation to the claims. The term "comprise/include" does not exclude the presence of elements or steps other than those listed in the claims. The word "a" or "an" in front of elements does not exclude the presence of a plurality of such elements. In device or system claims that enumerate several means or components, one or more of the means or components can be embodied in one and the same item of hardware. The mere fact that some measures are recited in dependent claims that are different from each other does not indicate that the combination of the measures cannot be used to advantage.

What is claimed is:

1. A medical data analysis method, comprising:

receiving a physical parameter of a subject that is associated with disease symptoms;

locating a semantic subspace of the subject in a medical data set by taking the physical parameter as a feature, comprising:

setting up a vector h according to the physical parameter of the subject to represent the physical parameter; and locating the semantic subspace of the subject in the medical data set by taking the physical parameter as a feature, wherein a matrix D is used to represent a collection of cases in a data set, $D=[D_1, D_2, \ldots, D_M]$, $D_i$ represents an i-th semantic subspace, $1 \leq j \leq M$, M represents the number of semantic subspaces, the locating comprising: acquiring X by an equation h=DX, wherein X is a coefficient vector indicative of the distribution of the vector h in each semantic subspace; and analyzing a probability $P_1$ of the subject being in a semantic subspace that the subject belongs to by analyzing semantic consistency associated with a particular disease of the semantic subspace where the physical parameter of the subject exists by judging the semantic consistency of the semantic subspace that the vector h is in;

analyzing a probability $P_2$ of the subject being in a node that the subject belongs to based on an evidence transference score of the physical parameter of the subject on a medical knowledge graph, wherein the evidence transference score is an evidence score passed from one node to another in the medical knowledge graph, comprising:

accessing the medical knowledge graph to obtain a portion of the medical knowledge graph in relation to the subject, the portion of the medical knowledge graph comprising a plurality of nodes $V=\{v_1, v_2, \ldots, v_N\}$ and an initial evidence score set $P_0=[P_{0,1}, P_{0,2}, \ldots, P_{0,N}]$ for said plurality of nodes, wherein N indicates the number of said plurality of nodes, $$\sum_{i=1}^{N} p_{0,i} = 1,$$

each node $v_i$ represents one physical parameter or one relevant category, i is an index for indexing the node, and $P_{0,i}$ represents the initial evidence score of the node $v_i$, determining a final evidence score set p for said plurality of nodes based on the evidence transference score of the physical parameter of the subject on the portion of the medical knowledge graph, and obtaining the probability $P_2$ of the subject being in the node that the subject belongs to based on a final evidence score of each node in the final evidence score set p, comprising: determining a probability of falling into each node by calculating a percentage of the final evidence score of each disease node in V in the sum of the final evidence scores of all disease nodes in V, and outputting the maximum probability in the probability as the probability $P_2$ of the subject being in the node that the subject belongs to; and determining a probability P of the subject being in the semantic subspace or node that the subject belongs to based on the probability $P_1$ and probability $P_2$:

$P = \alpha \times P_1 + (1-\alpha) \times P_2$, wherein $\alpha$ is a reconciling parameter used to adjust the proportion of P1 and P2, and $0 \leq \alpha \leq 1$.

2. The method according to claim 1, wherein the locating a semantic subspace of the subject in a medical data set by taking the physical parameter as a feature further comprises:

solving the equation h=DX by way of a sparsest solution to thereby determine the semantic subspace where the subject exists; and determining which semantic subspace has the most contents of h according to a value of each element in the coefficient vector X, thereby determining which semantic subspace h is most likely in.

3. The method according to claim 2, wherein the sparsest solution comprises:

solving $x^* = \arg\min \|X\|_1$ wherein X satisfies $\|DX-h\|_2 \leq \varepsilon$, and wherein $\|\cdot\|_1$ is L1 paradigm, $\|\cdot\|_2$ is L2 paradigm, and $\varepsilon$ is a predetermined parameter, wherein cases corresponding to non-zero dimensions in the obtained solutions $x^*$ constitute the semantic subspace that h is in.

4. The method according to claim 1, wherein the analyzing a probability P1 of the subject being in a semantic subspace that the subject belongs to by analyzing the semantic consistency associated with a particular disease of the semantic subspace where the physical parameter of the subject exists by judging the semantic consistency of the semantic subspace that the vector h is in further comprises:

calculating the semantic consistency between the semantic subspace that h is in and the semantic subspace $D_i$ by the following equations:

$$C_i = \frac{\|h_i\|_2^2}{\sum_j \|h_j\|_2^2 + \|\eta\|_2^2} (i = 1, 2, \ldots, M)$$

$$C_\eta = \frac{\|\eta\|_2^2}{\sum_j \|h_j\|_2^2 + \|\eta\|_2^2}$$

wherein $h=h_1+h_2+\ldots+h_M+\eta$, $h_i=D\delta_i(X)$, $\eta$ is an error, $\delta_i(X)$ represents a column vector obtained by multiplying elements of the coefficient vector X belonging to the dimensions of the semantic subspace $D_i$ by 1 and multiplying those belonging to the rest dimensions by 0.

5. The method according to claim 4, further comprises:

outputting the maximum value of $C_1, C_2, \ldots, C_M, C_\eta$ as the probability $P_1$ of the subject being in the semantic subspace that the subject belongs to.

6. The method according to claim 1, wherein the determining the final evidence score set p for said plurality of nodes further comprises:

performing iterative computation by the following equation to determine the final evidence score set p for said plurality of nodes:

$p_t = (1-d) \times p_0 + d \times p_{t-1} \times W,$ wherein d is a damping coefficient, $0 < d < 1$;

$$W = \begin{bmatrix} l_{11} & l_{12} & \cdots & l_{1N} \\ l_{21} & l_{22} & \cdots & l_{2N} \\ \vdots & \vdots & \cdots & \vdots \\ l_{N1} & l_{N2} & \cdots & l_{NN} \end{bmatrix}, l_{ij} = \frac{w_{i,j}}{\sum_{k=1}^{N} w_{i,k}},$$

$w_{i,j}$ represents a weight of an edge $e_{i,j}$ connecting nodes $v_i$, $v_j$ in V, $p_{t-1}$ and $p_t$ represent an evidence score set for said plurality of nodes before t iterative computation and that after t iterative computation respectively, the final evidence score set p is determined as $p_t$ after the iterative computation is terminated.

7. The method according to claim 6, wherein a condition for terminating the iterative computation is that $p_t$ does not change any longer or reaches a predetermined maximum number of iterations in the iterative computation.

8. The method according to claim 1, wherein the determining the final evidence score set p for said plurality of nodes further comprises:
   determining the final evidence score set p for said plurality of nodes by the following equation:

$$p=(1-d) \times P_0 \times (I - d \times W)^{-1},$$

wherein d is a damping coefficient, 0<d<1; I is an N×N unit matrix, $$W = \begin{bmatrix} l_{11} & l_{12} & \cdots & l_{1N} \\ l_{21} & l_{22} & \cdots & l_{2N} \\ \vdots & \vdots & \cdots & \vdots \\ l_{N1} & l_{N2} & \cdots & l_{NN} \end{bmatrix}, \quad l_{ij} = \frac{w_{i,j}}{\sum_{k=1}^{N} w_{i,k}},$$

$w_{i,j}$ represents a weight of an edge $e_{i,j}$ connecting the nodes $v_i$, $v_j$ in V.

9. A medical data analysis device, comprising:
   a memory configured to store computer executable instructions; and
   a processor coupled to the memory, which is configured to execute the computer executable instructions and thus cause the processor to carry out the method according to claim 1.

10. A medical data analysis device, comprising:
   a memory configured to store computer executable instructions; and
   a processor coupled to the memory, which is configured to execute the computer executable instructions and thus cause the processor to carry out the method according to claim 1.

11. A medical data analysis device, comprising:
   a memory configured to store computer executable instructions; and
   a processor coupled to the memory, which is configured to execute the computer executable instructions and thus cause the processor to carry out the method according to claim 1.

12. A computer-readable non-transitory storage medium, in which computer readable instructions are stored, the instructions, when executed by a computing device, causing the computing device to carry out the method according to claim 1.

13. A computer-readable non-transitory storage medium, in which computer readable instructions are stored, the instructions, when executed by a computing device, causing the computing device to carry out the method according to claim 1.

14. A computer-readable non-transitory storage medium, in which computer readable instructions are stored, the instructions, when executed by a computing device, causing the computing device to carry out the method according to claim 1.

15. A medical data analysis device, comprising:
   a receiver configured to receive a physical parameter of a subject that is associated with disease symptoms, and set up a vector h according to the physical parameter to represent the physical parameter;
   a subspace locator configured to locate a semantic subspace of the subject in a medical data set by taking the physical parameter as a feature, and acquire X by an equation h=DX, wherein D is a matrix used to represent a collection of cases in a data set, D=[D1, D2, ..., DM], Di represents and i-th semantic subspace, 1≤i≤M, M represents the number of semantic subspaces, and X is a coefficient vector indicative of distribution of the vector h in each semantic subspace; and
   a first analyzer configured to analyze a probability $P_1$ of the subject being in a semantic subspace that the subject belongs to by analyzing semantic consistency associated with a particular disease of the semantic subspace where the physical parameter of the subject exists by judging the semantic consistency of the semantic subspace that the vector h is in;
   a second analyzer configured to analyze a probability $P_2$ of the subject being in a node that the subject belongs to based on an evidence transference score of the physical parameter of the subject on a medical knowledge graph, wherein the evidence transference score is an evidence score passed from one node to another in the medical knowledge graph, comprising:
      an accessor configured to access the medical knowledge graph to obtain a portion of the medical knowledge graph in relation to the subject, the portion of the medical knowledge graph comprising a plurality of nodes V={$v_1, v_2, \ldots, v_N$} and an initial evidence score set $P_0$=[$P_{0,1}, P_{0,2}, \ldots, P_{0,N}$] for said plurality of nodes, wherein N indicates the number of said plurality of nodes $$\sum_{i=1}^{N} p_{0,i} = 1,$$

each node $v_i$ represents one physical parameter or one relevant category, i is an index for indexing the node, and $P_{0,i}$ represents the initial evidence score of the node $v_i$,
   a third analyzer configured to determine a final evidence score set p for said plurality of nodes based on the evidence transference score of the physical parameter of the subject on the portion of the medical knowledge graph, and
   a determiner configured to obtain the probability $P_2$ of the subject being in a node that the subject belongs to based on the final evidence score of each node in the final evidence score set p; and
   a reconciler configured to determine the probability P of the subject being in the semantic subspace or node that the subject belongs to based on the probability $P_1$ and probability $P_2$:
   $P = \alpha \times P_1 + (1-\alpha) \times P_2$, wherein $\alpha$ is a reconciling parameter used to adjust the proportion of P1 and P2, and 0≤α≤1.

* * * * *